United States Patent [19]

Power et al.

[11] Patent Number: 5,722,972
[45] Date of Patent: Mar. 3, 1998

[54] METHOD AND APPARATUS FOR ABLATION OF ATHEROSCLEROTIC BLOCKAGE

[76] Inventors: John A. Power, 202 Springhouse La., Pittsburgh, Pa. 15238; Mark Schmidhofer, 6550 Beacon St., Pittsburgh, Pa. 15217

[21] Appl. No.: 523,743

[22] Filed: Sep. 5, 1995

Related U.S. Application Data

[63] Continuation of Ser. No. 105,182, Aug. 12, 1993, abandoned.

[51] Int. Cl.⁶ ............................................. A61B 17/36
[52] U.S. Cl. ........................................... 606/7; 606/16
[58] Field of Search ............................ 606/1, 7, 10, 11, 606/12, 15, 16, 17

[56] References Cited

U.S. PATENT DOCUMENTS

| | | | |
|---|---|---|---|
| 4,418,688 | 12/1983 | Loeb | 606/15 X |
| 4,445,892 | 5/1984 | Hussein et al. | 606/15 X |
| 4,718,417 | 1/1988 | Kittrell et al. | 606/15 |
| 4,747,405 | 5/1988 | Leckrone | 606/16 X |
| 5,041,109 | 8/1991 | Abela | 606/15 |
| 5,437,659 | 8/1995 | Leckrone | 606/7 |

*Primary Examiner*—Jennifer Bahr
*Assistant Examiner*—Sonya Harris-Ogugua
*Attorney, Agent, or Firm*—Clifford A. Poff

[57] ABSTRACT

There is provided an excimer laser catheter which also has at the distal end thereof a tip-deflecting wire, such as a relatively small-size balloon catheter, one which is located alongside and to one side of the laser catheter and is adapted to be used by being activated to cause the laser to be located eccentrically with respect to the lumen of the blood vessel which it has entered and to be directed at adjacently located plaque which the laser would otherwise miss. With equipment of this kind, it is possible to perform in many instances a satisfactory angioplasty essentially with the laser alone, without incurring the delays and the risks and other drawbacks involved in using the conventional adjunctive balloon-catheter angioplasty following laser angioplasty. An ultrasonic transducer and a catheter tip is used to determine the location and morphology of atherosclerotic blockage.

13 Claims, 10 Drawing Sheets

METHOD AND APPARATUS FOR ABLATION OF ATHEROSCLEROTIC BLOCKAGE

This application is a continuation of application Ser. No. 08/105,182, filed Aug. 12, 1993 now abandoned.

BACKGROUND OF THE INVENTION

1. Field of the Invention

This invention relates to the treatment of patients who are suffering the effects of atherosclerotic blockage. In one aspect, it relates to a novel kind of catheter, one which comprises both a laser means and adjacent thereto at the distal end thereof (and to one side thereof, rather than surrounding) a relatively small-size balloon means, and in another aspect, the invention relates to a method for ablating plaque adhering to one side of the lumen of a blood vessel, which comprises inflating the aforementioned balloon means to position the laser means so that its energy may be directed against the plaque and then activating the aforementioned laser means. By providing and using equipment in accordance with the invention, it becomes possible to conduct a treatment for atherosclerotic blockage which is advantageous in comparison with what has hitherto been known, in that there are avoided (a) the danger of possibly closing the blood vessel due to cracking or fissuring of the plaque by expanding a larger-size balloon catheter therein and (b) the difficulty that plaque tends to re-form at the sites where the more conventional balloon angioplasty has been conducted; equipment according to the invention makes it possible to provide a treatment which amounts for all practical purposes to laser angioplasty alone, without reliance upon a balloon means for increasing the dimensions of the unblocked or unimpeded portion of the cross-sectional area of the blood vessel being treated.

2. Description of the Prior Art

Even in the late 1960's it was known that it is possible to overcome the effects of atherosclerotic blockage in the coronary arteries of the heart by performing a coronary-bypass operation, using, for example, a blood vessel harvested from the patient's leg and suitably connecting it to the heart. This is, of course, a very serious operation and one that requires a long period of recuperation.

In the late 1970's, there was introduced by Dr. Gruntzig the idea of balloon catheter angioplasty. In this procedure, a catheter having at its distal end a balloon means is introduced into the patient's leg or arm and is steered to a desired location in the heart, adjacent to a section of blood vessel which contains a deposit of plaque which is obstructing the lumen, the open space of the blood vessel. The balloon is expanded, then contracted and withdrawn. In the case of the treatment of a relatively large vessel, it may be necessary to repeat the procedure with a larger balloon means. This procedure has the advantage of avoiding the performance of open-heart surgery with its attendant risks and difficulties, but presents the difficulty that in at least some cases, upwards of 5%, the procedure is a complete failure because the balloon angioplasty causes a closure of the vessel being treated, which makes necessary a very serious emergency operation. This procedure also has the drawback that plaque tends to re-form at the site which has been treated with conventional balloon angioplasty.

More recently, there has been developed a kind of angioplasty which employs a laser catheter. ELCA (Excimer Laser Coronary Angioplasty) is used to treat patients who are having angina or a heart attack due to a blockage in a coronary artery which supplies blood and oxygen to heart muscle. A long tube (guiding catheter) is inserted into an artery in the leg or arm and travels up the artery to the heart. The guiding catheter is then directed into one of the coronary arteries having a blockage in it. Next, a guidewire is placed within the guiding catheter and is worked across the blockage. Following this, a laser catheter is slid over the guidewire and up to the blockage, at which point the laser is turned on to vaporize the blockage. The laser catheter is then removed.

At least about 85 percent of the time, ELCA requires subsequent adjunctive balloon dilatation to achieve adequate opening of blocked coronary arteries. Most of the coronary arteries which develop significant blockages have an internal diameter of 2 to 4 millimeters (0.079 to 0.157 inch). At present, the maximal diameter of most laser catheters is between 1.7 and 2.0 millimeters.

It is known, for example, from the Leary patent, U.S. Pat. No. 4,545,390, that it is possible to produce a guide wire, such as one made of a platinum-tungsten alloy, and after introducing it into the body in either the leg (the femoral artery) or the shoulder (the brachial artery), to steer it to the patient's heart. Leary describes a guide wire which is of very small diameter (under 0.020 inch) and has a distal portion which is tapered and surrounded by a helically wound spring brazed at or near its ends to the ends of the tapered portion, one segment of the spring extending beyond the end of the guide wire to serve as a highly flexible bumper and prevent the end of the guide wire from causing traumatic injury to the blood vessel through which it passes. The guide wire is radio-opaque, which makes it possible to follow its progress fluoroscopically during any procedure in which it is employed.

U.S. Pat. No. 4,646,742, to Packard et al., discloses a percutaneous transluminal angioplasty catheter which has a balloon means at its distal end and also, in one embodiment, affords equipment having a laser means at the distal end, adjacent to the balloon means. This patent fails to teach or suggest, however, the idea of having the balloon catheter means be of relatively small size and located to one side of the catheter, so that when the balloon means is expanded, the laser means is positioned so that its energy is directed at plaque located eccentrically of the lumen of the blood vessel, on the side of the lumen of the blood vessel which is opposite to the balloon means, and, of course, it also correspondingly lacks any teaching or appreciation of a reason for providing such equipment, such as to enable laser angioplasty to be conducted without need for subsequent adjunctive balloon angioplasty and without thereby incurring the disadvantages of conventional balloon angioplasty, namely, risk of closure due to cracking or fissuring of a large volume of plaque at the site treated.

SUMMARY OF THE INVENTION

There is provided an excimer laser catheter which also has at the distal end thereof a tip-deflecting means, such as a relatively small-size balloon catheter means, one which is located alongside and to one side of the laser catheter means and is adapted to be used by being activated to cause the laser means to be located eccentrically with respect to the lumen of the blood vessel which it has entered and to be directed at adjacently located plaque which the laser means would otherwise miss. With equipment of this kind, it is possible to perform in many instances a satisfactory angioplasty essentially with the laser means alone, without incurring the delays and the risks and other drawbacks involved in using the conventional adjunctive balloon-catheter angioplasty means following laser angioplasty.

BRIEF DESCRIPTION OF THE DRAWINGS

A complete understanding of the invention may be obtained from the foregoing and following description thereof, taken in conjunction with the appended drawings, in which.

DETAILED DESCRIPTION OF THE PREFERRED EMBODIMENTS

Figure 1:
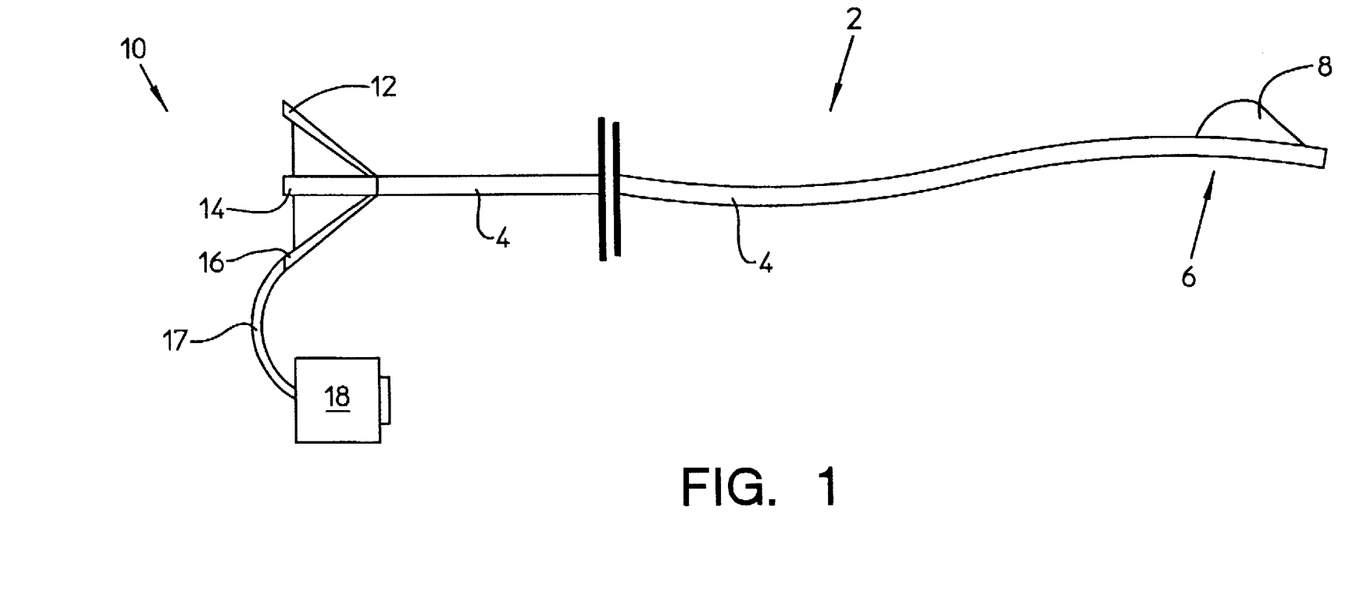
FIG. 1 is an overall view of a complete catheter in accordance with one embodiment of the present invention.
Figure 2:
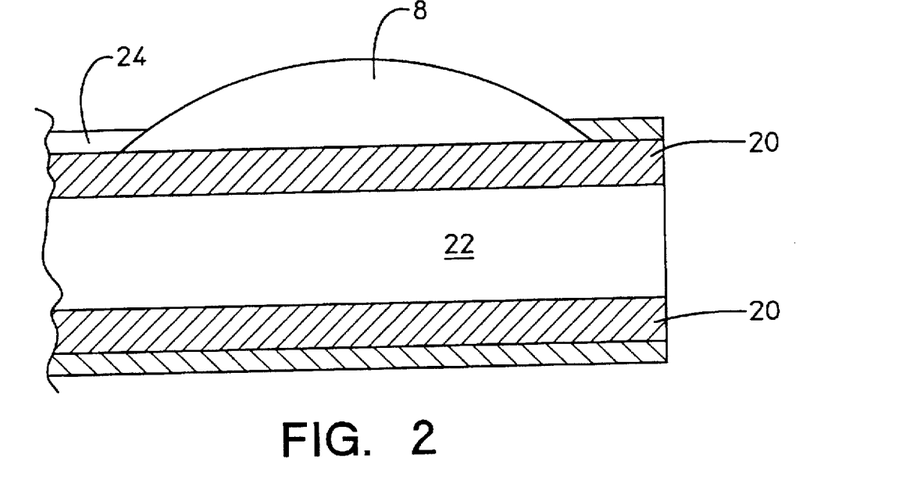
FIG. 2 is a side view of a distal end portion of a catheter in accordance with the embodiment of the present invention shown in FIG. 1, the balloon thereof being in the inflated condition.
Figure 3:
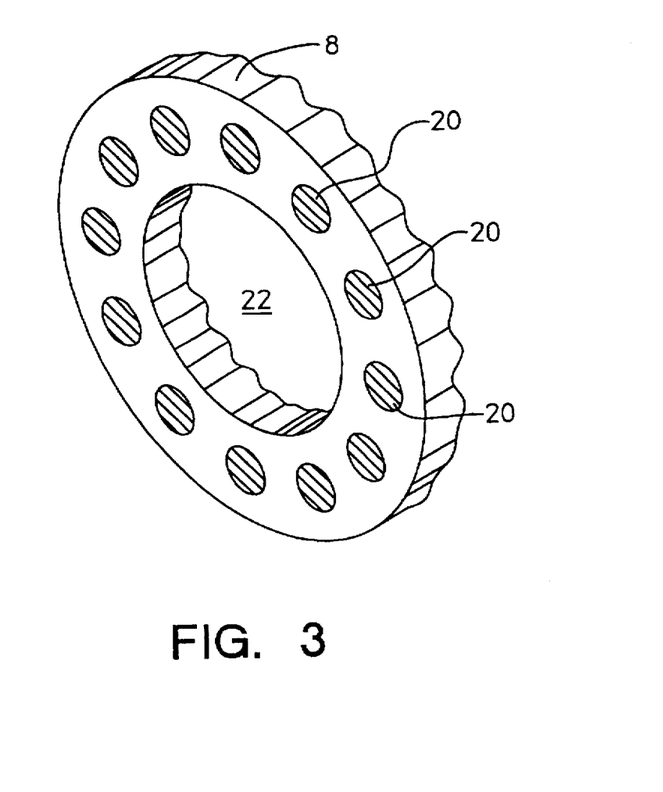
FIG. 3 is an end view of the same distal portion of a catheter in accordance with the embodiment of the present invention shown in FIG. 1, the balloon thereof being in the deflated condition.

One embodiment of laser catheter means according to the present invention is illustrated in FIGS. 1 to 3. The catheter, indicated generally at 2, comprises an elongated main body portion 4 which, in accordance with a principal feature of the present invention, terminates in a distal end 6 which includes a balloon means 8 located alongside the catheter and adapted to serve to move it eccentrically of the blood-vessel lumen in which it is used. The proximal end 10 of the catheter 2 contains such features as a balloon-inflation port 12, a port 14 for the insertion of a guidewire, and a port 16 for introducing to the catheter the fiber-optics laser means 17, which is connected to a hookup to a laser generator, indicated generally at 18.

In this embodiment of the invention, as is shown essentially diagramatically in FIGS. 2 and 3, the catheter 2 has a plurality of fiber members 20 which are arranged to surround a central lumen 22, which serves for the passage of a guidewire (not shown, but one which is steerable in a manner familiar to those skilled in the art to direct the distal end 6 of the catheter 2 to a site of intended use). The balloon means 8, indicated in its expanded condition in FIG. 2 and in its deflated condition in FIG. 3, is inflatable by means of a balloon-inflation channel indicated at 24. For purposes of illustration, the catheter 2 is envisaged as having an overall diameter of 1.7 millimeters, a figure which may, within limits, be increased or decreased as desired to suit the requirements of its intended use.

Figure 4:
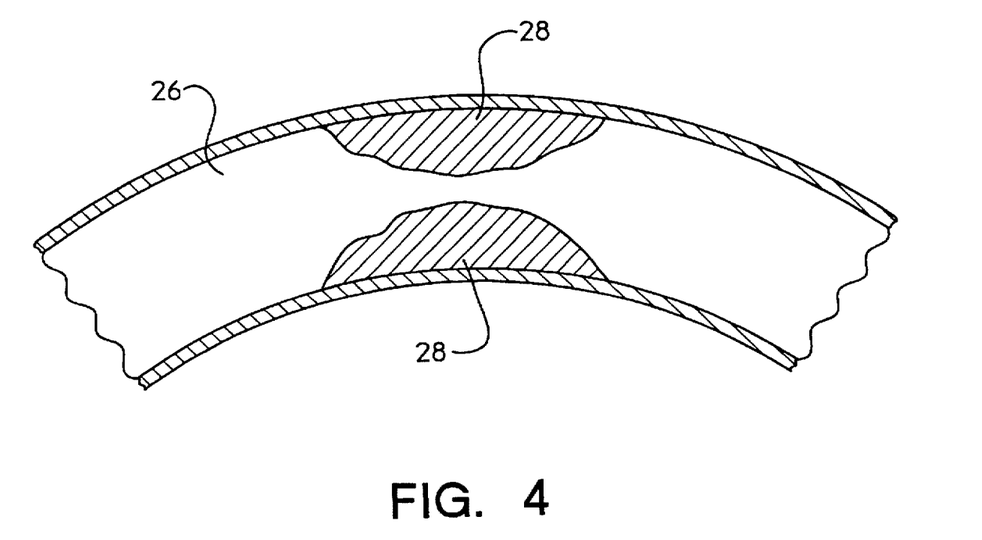
FIGS. 4 to 16 are a set of diagrams depicting a section of stenosed artery and the sequential changes in its condition as it is acted upon by a catheter in accordance with the embodiment of the present invention shown in FIG. 1.
Figure 5:
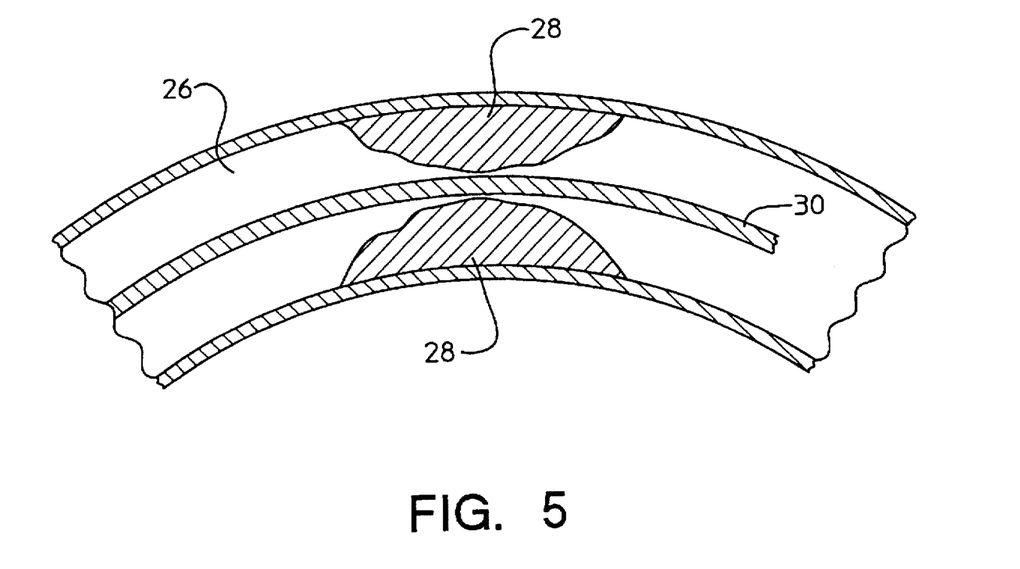
Figure 6:
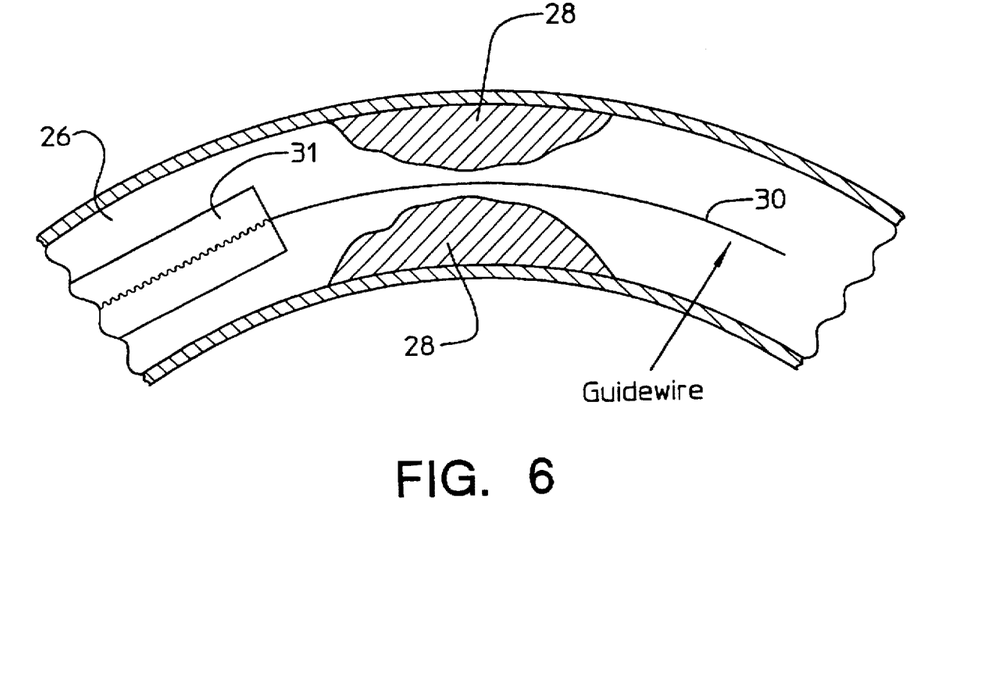
Figure 7:
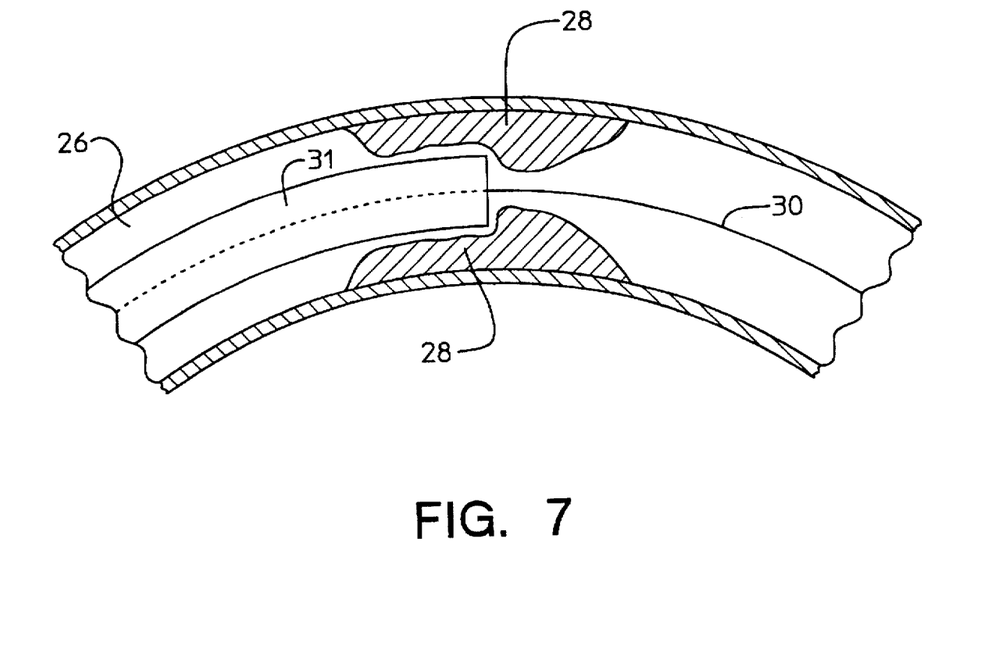
Figure 8:
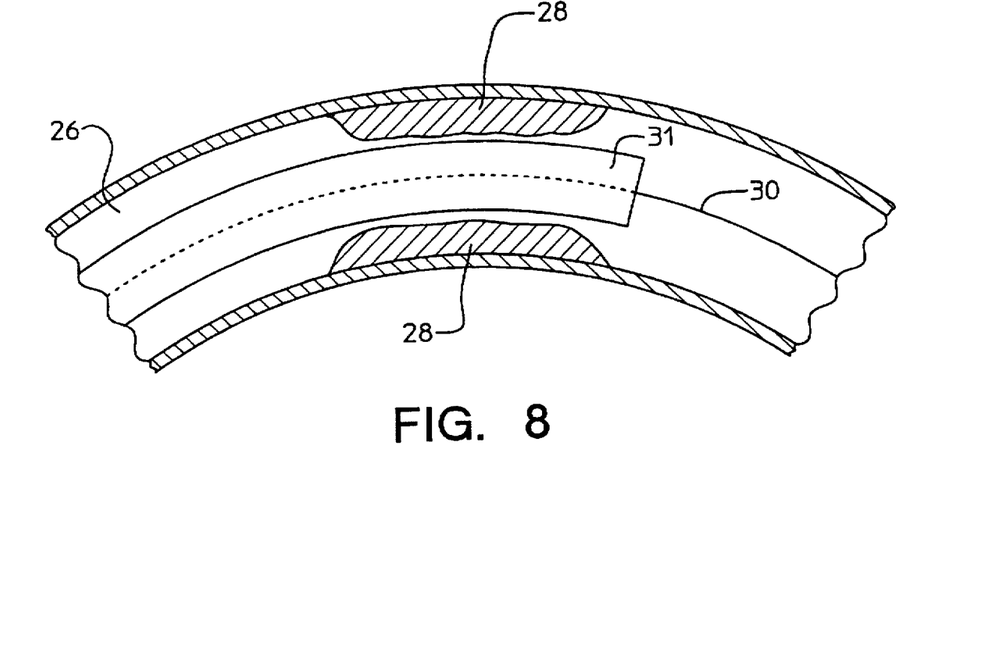
Figure 9:
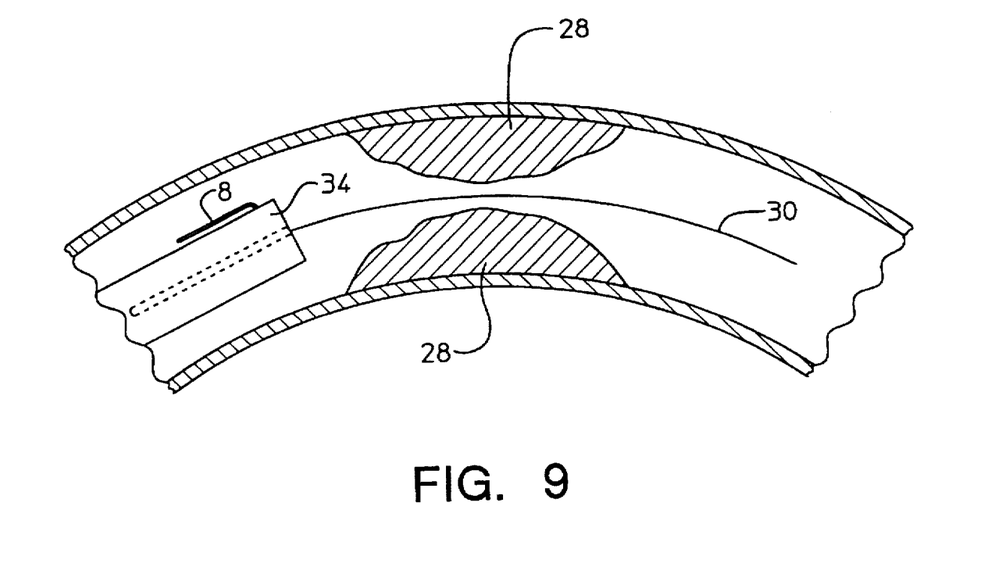
Figure 10:
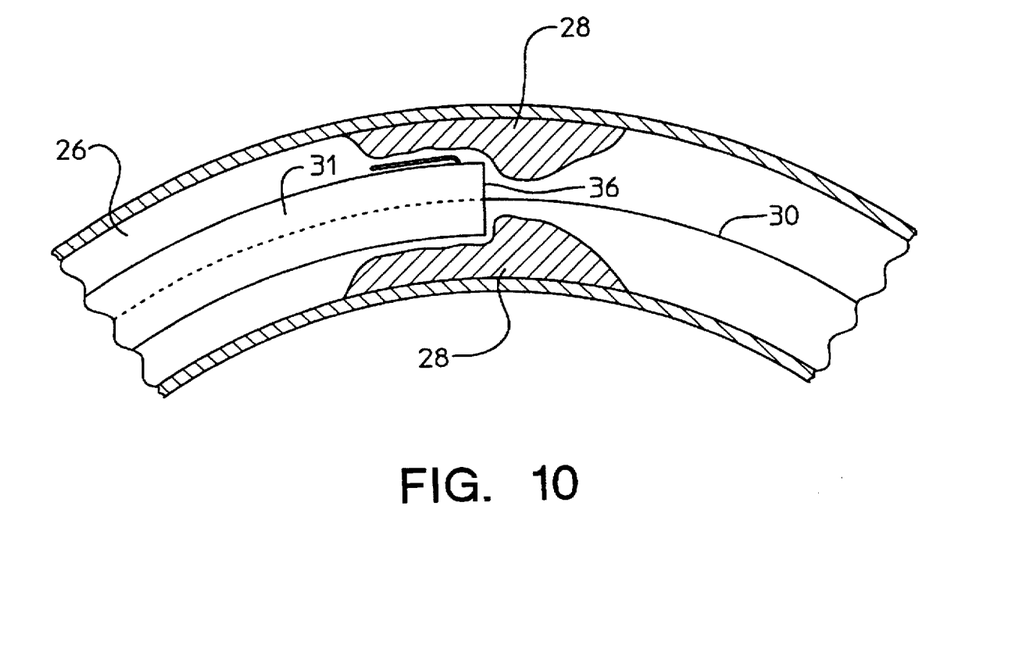
Figure 11:
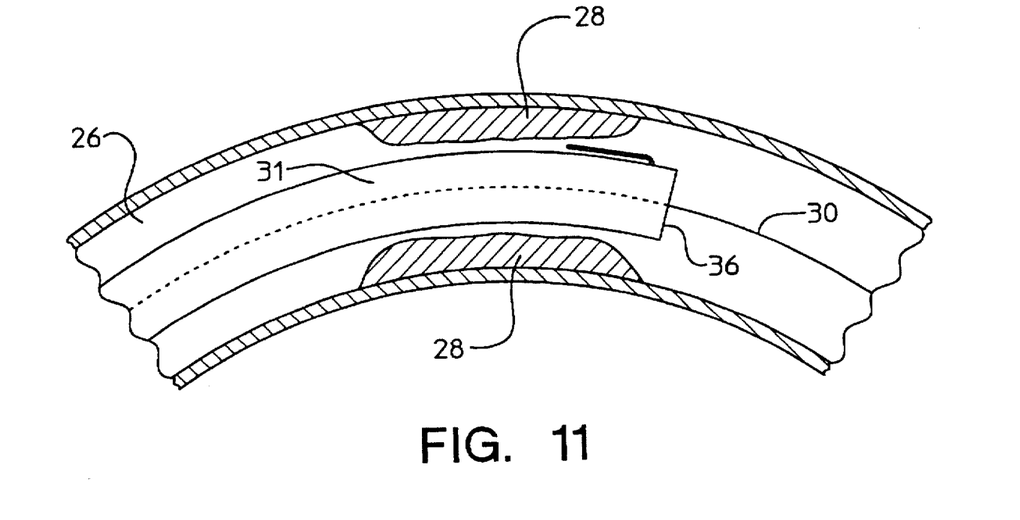
Figure 12:
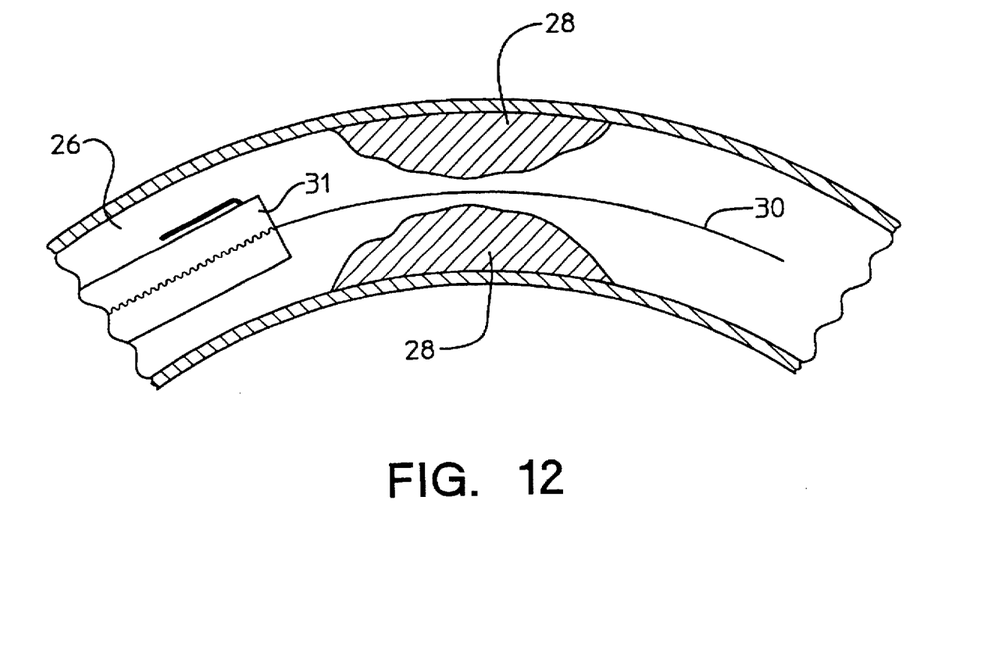
Figure 13:
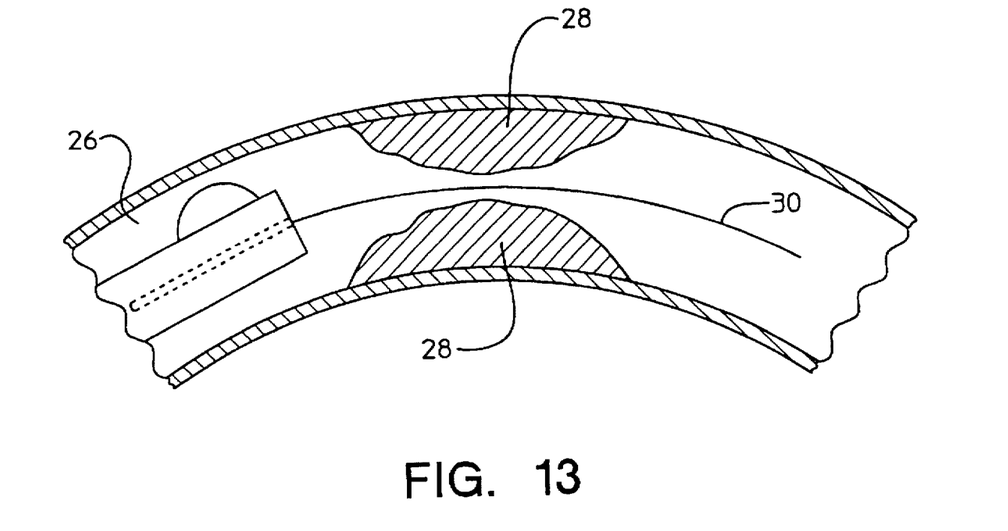
Figure 14:
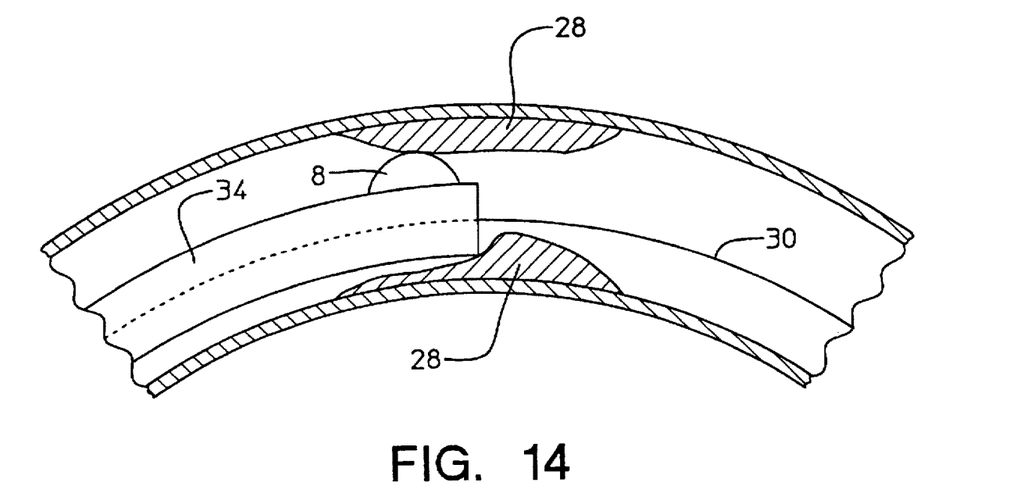
Figure 15:
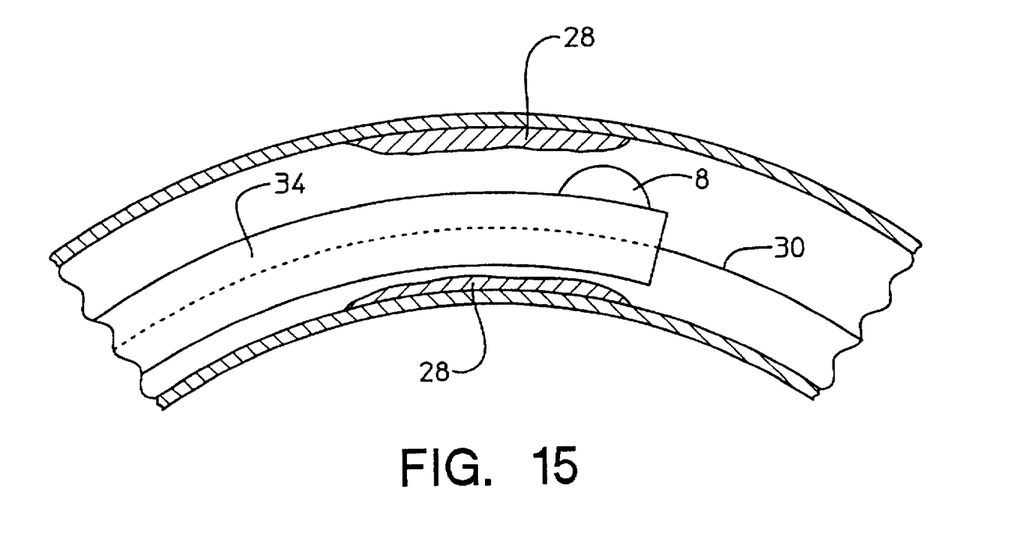

For purposes of comparison and to provide a suitable introduction to an explanation of the use of the present invention, FIGS. 4 to 8 illustrate the use of a laser catheter to treat an instance of vascular stenosis in accordance with what has been known in the prior art. FIG. 4 shows a portion 26 of blood vessel which is shown as having atherosclerotic blockage therein at 28, and FIG. 5 shows the situation after a steerable guidewire 30 has been caused to traverse the location of the atherosclerotic blockage. FIGS. 6 to 8, inclusive, illustrate the situation respectively before, during, and after the catheter 31 has come into contact with the atherosclerotic blockage 28. It is to be understood that the catheter 31 may or may not be one which is in accordance with the present invention. FIGS. 4 to 8 illustrate how even a conventional laser catheter may be used to effect a pass through an instance of atherosclerotic blockage with the laser catheter remaining substantially centrally located with respect to the lumen of the blood vessel which it travels, an operation which, while it may in certain circumstances effect some sufficient opening of the stenosed blood vessel, nevertheless leaves behind a certain portion of atherosclerotic blockage which it would be desirable to remove.

Figure 16:
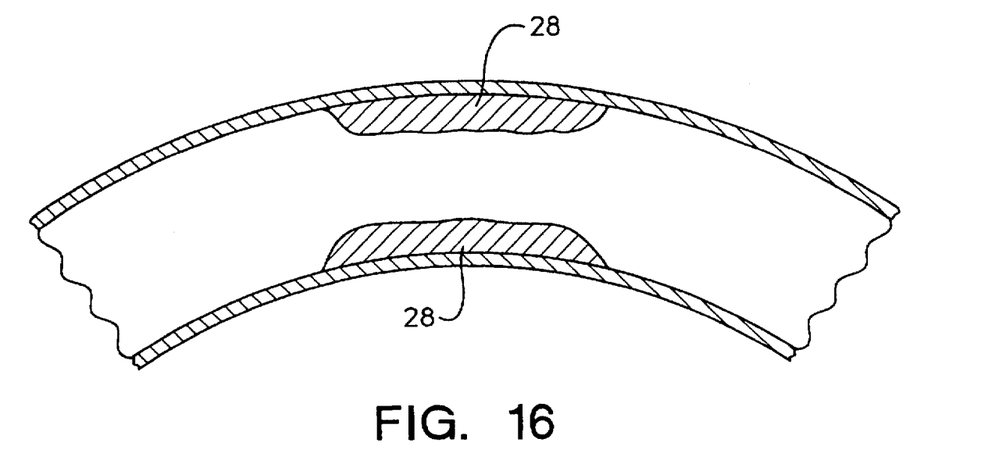

In accordance now with the present invention, there is preferably to be practiced a method which is more particularly indicated in FIGS. 9 to 16. In the FIGS. 9 to 16, there is, as before, indicated a blood-vessel portion 26 having therein atherosclerotic blockage 28. In accordance with the method of the present invention, there is first made a pass of a laser catheter means 34, one which corresponds to the laser catheter means 2 hereinabove, along the steerable guidewire 30 and through the area of atherosclerotic blockage 28, with the balloon means 8 of the catheter 34 in its deflated condition (FIG. 9 to 11, inclusive), following which the laser catheter 34 is withdrawn so that its distal end 36 is brought to a location on the side of the blockage 28 which is toward the proximal end of the catheter 34 (see FIG. 12). Then, the balloon means 8 is inflated (FIG. 13) in order to displace the distal end 36 of the laser catheter 34 eccentrically within the lumen of the blood-vessel portion 26, and then (see FIGS. 14 and 15) another pass is made with the laser catheter 34 through the area of atherosclerotic blockage 28, this time with the balloon means 8 causing the laser catheter means 34 to operate upon and ablate (remove) some further portion of the atherosclerotic blockage that the laser catheter otherwise would have missed. FIG. 16 indicates the condition of the region of atherosclerotic blockage 28 at the completion of the procedure. Most of the blockage has been removed that can be done with a single pass of a laser catheter of a given size when the laser catheter remains centrally located within the blood-vessel lumen, and any remaining blockage or plaque after conducting excimer laser coronary angioplasty is left with a relatively smooth surface, which offers less opportunity for affording sites and surface for the re-formation of blockage or plaque.

Figure 17:
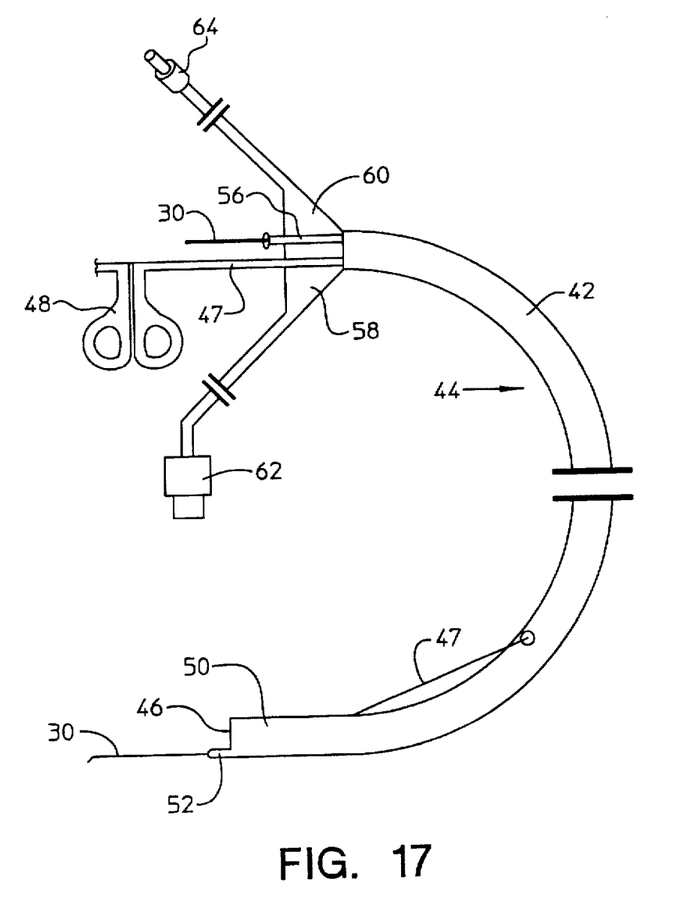
FIGS. 17 and 18 are, respectively, an overall view of a complete catheter in accordance with a second embodiment of the present invention and an end view of the distal portion of the same.
Figure 18:
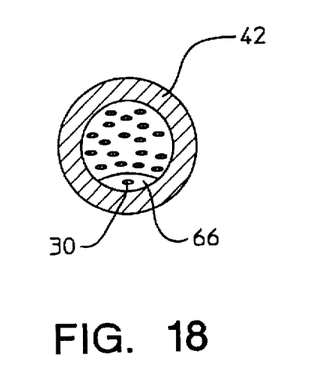

Another embodiment of laser catheter means according to the present invention is illustrated in FIGS. 17 and 18. The catheter, indicated generally at 42, comprises an elongated main body portion 44 which, in accordance with a principal feature of the present invention, terminates in a distal end 46 which includes a somewhat different means which is adapted to serve to move it eccentrically of the blood-vessel lumen in which it is used. In the embodiment of the present invention shown in FIGS. 17 and 18, there is provided a tip-deflection wire 47, a main portion of which, it will be understood, traverses the main body portion 44 of the catheter interiorly of said catheter, preferably but not necessarily contained in a lumen (not shown) for receiving the said tip-deflection wire. As shown in FIG. 17, however, the tip-deflection wire 47 also contains a portion adjacent to its distal end wherein it travels exteriorly of the catheter 42, with the distal end of tip-deflection wire 47 being suitably secured (by means not shown) to the distal end of the catheter 42. Moreover, at the proximal end of the tip-deflection wire 47, there is provided a handle 48 for pulling upon the tip-deflection wire 47 in order to activate it, for purposes the same as has been indicated above with respect to the balloon means 8, i.e., to cause the distal end of the catheter to become located eccentrically with respect to the lumen of the blood vessel in which it is located and thereby enable the catheter to attack a portion of the atherosclerotic blockage that would otherwise be missed.

In the embodiment of the invention depicted in FIGS. 17 and 18, the distal end 50 of the laser catheter 34 includes an ultrasonic transducer indicated at 52, and thus the proximal end 54 of the catheter 42 contains, in addition to the port 56 through which there is introduced the steerable guidewire 30 and the port 58 for the cable of fibers bearing laser light, a port 60 associated with the ultrasound equipment. Indicated at 62 and 64 are, respectively, plugs for interfacing with appropriate laser and ultrasound equipment.

As can be seen in FIG. 18, the guidewire 30 preferably is provided with its own lumen 66.

It is especially advantageous to provide equipment which has both ultrasound equipment and means for locating the laser catheter head eccentrically of the blood-vessel lumen containing the blockage, because this is what is needed for an optimally useful and efficient apparatus: the ultrasound means affords a particularly accurate indication of the location and morphology of the plaque or blockage, and the means for moving the laser catheter head eccentrically is necessary in order that the laser means may then be brought exactly into the correct position to affect and ablate the blockage which the ultrasound system has made it possible to sense.

Figure 19:
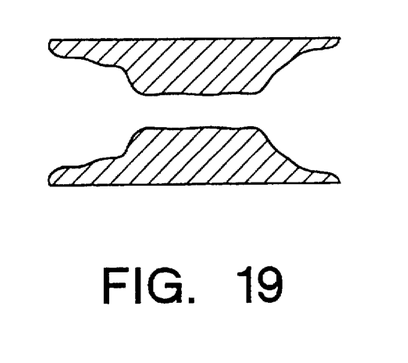
FIGS. 19 and 20 are diagrammatic representations of the difference between atherosclerotic blockage which has been treated in accordance with the present invention (FIG. 19) as opposed to the prior art (FIG. 20).
Figure 20:
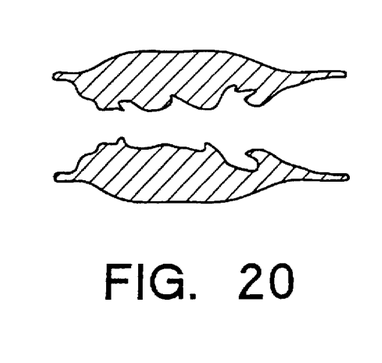

It must be emphasized in treating instances of atherosclerotic blockage as much plaque as possible must be removed. The point which is being made here is illustrated by reference to FIGS. 19 and 20. FIG. 19 indicates what the treated area formerly containing atherosclerotic blockage looks like in cross section immediately following the laser treatment, whereas FIG. 20 indicates what the corresponding cross-section looks like after a subsequent step of balloon angioplasty. It can be seen that after balloon angioplasty, there is left a condition which provides a considerable additional number of sites and surfaces for the attachment or formation of plaque or blockage, and in a preferred mode of practicing the present invention in its method aspects, this is precisely what it is desirable to avoid, thereby minimizing the likelihood of the necessity of a repeated treatment.

Although there have shown and described herein certain embodiments of the present invention, it is intended that there be covered as well hereby any change or modification in the said invention which can be made without departing from its spirit and scope.

GLOSSARY angioplasty—is the surgical repair of a blood vessel, as by inserting a balloon-tipped catheter to unclog it or by replacing part of the vessel.

ablate—is to remove or dissipate by melting, vaporization, erosion, etc.

ablation—is the act or process of ablating or the removal of organs, abnormal growths, or harmful substances from the body by mechanical means, as by surgery.

brachial—is belonging or pertaining to the arm, foreleg, wing, or pectoral fin of a vertebrate.

excimer—is a molecular complex of two, usu. identical, molecules that is stable only when one of them is in an excited state.

ischemia—is a local deficiency of blood supply produced by vasoconstriction or local obstacles to the arterial flow.

stenosis—is a narrowing or stricture of a vessel or passage of the body.

vascular—pertaining to, composed of, or provided with vessels that convey fluids, as blood or sap.

We claim:

1. An apparatus for ablation of atherosclerotic blockage, said apparatus including, in combination, a catheter including a tip or distal end adapted to be inserted into and guided within a blood vessel lumen to a site therein which contains atherosclerotic blockage, a forward firing excimer-laser fiber carried by the tip or distal end of said catheter to a site in the blood vessel lumen containing atherosclerotic blockage, an ultrasonic transducer in the proximal end of the catheter for determining the location and morphology of atherosclerotic blockage to be subsequently removed by said forward firing excimer laser fiber, and an actuator at a non-surrounding outer peripheral location on the catheter and entirely proximally located from the distal end of the laser fiber for deflecting said tip or distal end of said catheter, said actuator being actuatable externally at a side surface of the blood vessel lumen to displace said tip or distal end in the blood vessel lumen eccentrically away from the center and into a generally parallel relation with the side of the blood vessel lumen containing atherosclerotic blockage having a location and morphology for removal by said forward firing excimer-laser.

2. An apparatus as defined in claim 1 wherein said actuator comprises a tip-deflecting wire and means for activating the tip deflecting wire.

3. An apparatus as defined in claim 1 wherein said actuator includes a balloon having a dimension and a location as to be useful to direct radiation from excimer-laser fiber against plaque adhering to a portion of the blood vessel lumen opposite to the location of said balloon catheter means.

4. The apparatus according to claim 1 further including a plurality of said forward firing excimer-laser optical fiber arranged as an array about a central lumen in the catheter.

5. The apparatus according to claim 1 further including a guide wire for steering the tip or distal end of the catheter to a site of intended use.

6. A method of treating vascular stenosis including the steps of:

inserting a tip to distal end of a catheter within a blood vessel lumen to a site therein containing an atherosclerotic blockage;

displacing the tip or distal end of the catheter by a actuator at a non-surrounding outer peripheral location on the catheter and entirely proximately located from the distal end of a forward firing laser fiber eccentrically away from the center and into a generally parallel relation with the side of the blood vessel lumen containing the atherosclerotic blockage;

causing said excimer-laser to forward fire from a forward firing laser fiber carried by the tip or distal end of the catheter to remove a desired portion of said blockage.

7. The method according to claim 6 including the further step of using an ultra sound transducer to determine the shape and location of a quantity of atherosclerotic blockage to be removed and thereafter removing portion of the blockage by said step of causing an excimer-laser to forward fire.

8. The method according to claim 6 wherein said step of displacing the tip or distal end includes inflating a catheter balloon located in a non surrounding relation at an outer peripheral site on the tip or distal end of the catheter to position the same eccentrically and generally parallel with the side wall of the blood vessel lumen and thereafter removing portion of the blockage by said step of causing an excimer-laser to forward fire.

9. The method according to claim 8 wherein after said step of causing an excimer-laser to forward fire, the method includes the further steps of deflating the catheter balloon, repositioning the tip or distal end of the catheter with respect to the blood vessel lumen containing the instance of atherosclerotic blockage and thereafter repeating the steps of displacing the tip or distal end of the catheter and said step of causing an excimer-laser to forward fire.

10. The method according to claim 9 wherein after said step of causing an excimer-laser to forward fire the method includes the further step of using an ultra sound transducer to determine the shape and location of a quantity of atherosclerotic blockage to be removed and thereafter performing said steps of repositioning the tip or distal end of the catheter, displacing the tip or distal end of the catheter and causing an excimer-laser to forward fire.

11. The method according to claim 6 wherein said step of displacing the tip or distal end includes activating a tip deflecting wire which includes a portion thereof proximal to the tip or distal end of the catheter to position the same eccentrically and generally parallel with the side wall of the blood vessel lumen and thereafter removing portion of the blockage by said step of causing an excimer-laser to forward fire.

12. The method according to claim 11 wherein after said step of causing an excimer-laser to forward fire, the method includes the further steps of repositioning the tip or distal end of the catheter with respect to the blood vessel lumen containing the instance of atherosclerotic blockage and thereafter repeating the steps of displacing the tip or distal end of the catheter and said step of causing an excimer-laser to forward fire.

13. The method according to claim 12 wherein after said step of causing an excimer-laser to forward fire the method includes the further step of using an ultra sound transducer to determine the shape and location of a quantity of atherosclerotic blockage to be removed and thereafter performing said steps of repositioning the tip or distal end of the catheter, displacing the tip or distal end of the catheter and causing an excimer-laser to forward fire.

\* \* \* \* \*